United States Patent [19]

Marrese et al.

[11] Patent Number: 5,660,974

[45] Date of Patent: Aug. 26, 1997

[54] COLOR DEVELOPER CONTAINING HYDROXYLAMINE ANTIOXIDANTS

[75] Inventors: Carl Anthony Marrese, Penfield; Sucheta Tandon, Fairport; Robert James Perry, Pittsford; Lynda Woedy McGarry, North Chili, all of N.Y.

[73] Assignee: Eastman Kodak Company, Rochester, N.Y.

[21] Appl. No.: 448,075

[22] Filed: May 23, 1995

Related U.S. Application Data

[63] Continuation of Ser. No. 257,601, Jun. 9, 1994, abandoned.

[51] Int. Cl.$^6$ ................................................. G03C 7/413
[52] U.S. Cl. ........................... 430/490; 430/467; 430/486
[58] Field of Search ............................. 430/464, 467, 430/486, 490

[56] References Cited

U.S. PATENT DOCUMENTS

| | | | |
|---|---|---|---|
| 4,264,716 | 4/1981 | Vincent et al. | 430/380 |
| 4,717,748 | 1/1988 | Ravichandran et al. | 564/301 |
| 4,798,783 | 1/1989 | Ishikawa et al. | 430/372 |
| 4,800,153 | 1/1989 | Morimoto et al. | 430/380 |
| 4,801,516 | 1/1989 | Ishikawa et al. | 430/380 |
| 4,814,260 | 3/1989 | Koboshi et al. | 430/464 |
| 4,853,318 | 8/1989 | Fujita et al. | 430/380 |
| 4,897,339 | 1/1990 | Andoh et al. | 430/372 |
| 4,965,176 | 10/1990 | Ishikawa et al. | 430/378 |
| 4,966,834 | 10/1990 | Ishikawa et al. | 430/393 |
| 4,978,786 | 12/1990 | Messina et al. | 564/160 |
| 5,071,734 | 12/1991 | Ueda et al. | 430/372 |
| 5,110,713 | 5/1992 | Yoshida et al. | 430/372 |
| 5,153,108 | 10/1992 | Ishikawa et al. | 430/372 |
| 5,173,395 | 12/1992 | Asami | 430/376 |
| 5,262,563 | 11/1993 | Morimoto | 562/104 |

FOREIGN PATENT DOCUMENTS

| | | |
|---|---|---|
| 0 411 513 A1 | 2/1991 | European Pat. Off. |
| 0 439 142 A1 | 7/1991 | European Pat. Off. |
| 0 545 645 A1 | 6/1993 | European Pat. Off. |
| 2638525 | 3/1977 | Germany |

*Primary Examiner*—Hoa Van Le
*Attorney, Agent, or Firm*—Sarah Meeks Roberts; J. Lanny Tucker

[57] ABSTRACT

A composition for developing a silver halide color photographic material comprising a color developing agent and a hydroxylamine compound represented by Formula I or II:

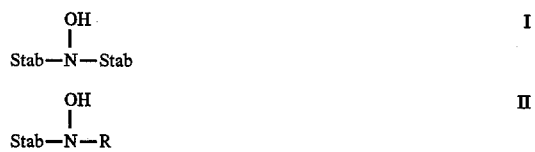

wherein Stab is a stabilizing group such that when the hydroxylamine compound is added to a test developer solution of the following formula the pH of the test developer solution decreases less than 0.12 at an aeration time of 90 hours:

TABLE 1

| Developer Formulation | |
|---|---|
| Components | Quantity/L |
| Lithium salt of sulfonated Polystyrene (30% wt/wt Liq) | 0.25 mL |
| Triethanolamine | 11.0 mL |
| Stilbene Stain-Reducing Agent | 2.3 g |
| Hydroxylamine compound | 0.05 moles |
| Lithium Sulfate | 2.7 g |
| 1-Hydroxyethylidene-1-diphosphonic acid (60% wt/wt Liq) | 0.8 mL |
| Potassium Chloride | 1.8 g |
| Potassium Bromide | 0.2 g |
| 4-amino-3-methyl-N-ethyl-N-(β-methanesulfonamidoethyl)aniline (color developer) | 4.85 g |
| Potassium Carbonate | 25.0 g |
| Water to 1 L solution pH adjusted to 10.12 with KOH | | and wherein R is a substituted or unsubstituted alkyl, aryl or heterocyclic group bonded to N by a carbon atom.

19 Claims, 4 Drawing Sheets

COLOR DEVELOPER CONTAINING HYDROXYLAMINE ANTIOXIDANTS

REFERENCE TO RELATED APPLICATION

This application is a continuation of U.S. Ser. No. 08/257,601, filed Jun. 9, 1994, now abandoned.

BACKGROUND OF THE INVENTION

This invention relates to the processing of silver halide color photographic materials, and more specifically to color developer solutions containing new preservatives, or antioxidants, that improve the stability of the developer solution.

Color developers, such as, 4-amino-3-methyl-N-(β-methanesulfonamidoethyl)aniline, are reducing agents, and are quite susceptible to aerial oxidation, i.e., oxidation by dissolved oxygen. To alleviate this problem, color developers generally contain an antioxidant, or preservative, to preserve the oxidation state of the color developer and maintain useful color developer activity.

Many classes of compounds have been employed as color developer solution antioxidants, e.g., hydroxylamines, hydroxamic acids, oximes, nitroxy radicals, hydrazines, hydrazides, phenols, saccharides, monoamines, diamines, tertiary amines, polyamines, quartinary ammonium salts, alpha-hydroxy ketones, alcohols, diamides, and disulfonamides. To be practical, antioxidants must be soluble in aqueous media, non-toxic to living organisms, low cost, and non-silver halide developers. Further, it is desirable that antioxidants react slowly with oxygen and rapidly with oxidized color developer, but not so rapidly that color development is retarded. These considerations greatly limit the number and class of compounds that can be used as practical antioxidants in color developer solutions.

The compounds most often employed as photographic color developer preservatives, or antioxidants, are the hydroxylamines. Hydroxylamines exhibit excellent characteristics as color developer antioxidants. Their rate of aerial oxidation is slow, they are not good silver halide developers, and they are relatively inexpensive to produce. Examples of hydroxylamines which have been used in color developers can be found in U.S. Pat. Nos. 4,978,786; 4,800,153; 4,801,516; 4,814,260; 4,965,176; 4,966,834; and 5,071,734.

Unfortunately, many hydroxylamines, both mono-and di-substituted, have significant vapor pressure at room and processing temperatures, and yield an "amine like", or unpleasant, odor. Other hydroxylamines do not meet the stability requirements for a color developer. To prolong developer activity the antioxidant must also be stable when it has undergone oxidation by oxygen, or, as a result of its preserving action, reaction with oxidized color developer. There is still a need for a hydroxylamine antioxidant which is odorless and which is stable after it undergoes oxidation.

SUMMARY OF THE INVENTION

This invention provides a composition for developing a silver halide color photographic material comprising a color developing agent and a hydroxylamine compound represented by Formula I or II:

wherein Stab is independently a stabilizing group such that when the hydroxylamine compound is added to a test developer solution of the following formula the pH of the test developer solution decreases less than 0.12 at an aeration time of 90 hours

| Components | Quantity/L |
| --- | --- |
| Lithium salt of sulfonated Polystyrene (30% wt/wt Liq) | 0.25 mL |
| Triethanolamine | 11.0 mL |
| Stilbene Stain-Reducing Agent | 2.3 g |
| Hydroxylamine compound | 0.05 moles |
| Lithium Sulfate | 2.7 g |
| 1-Hydroxyethylidene-1-diphosphonic acid (60% wt/wt Liq) | 0.8 mL |
| Potassium Chloride | 1.8 g |
| Potassium Bromide | 0.2 g |
| 4-amino-3-methyl-N-ethyl-N-(β-methanesulfonamidoethyl)aniline (color developer) | 4.85 g |
| Potassium Carbonate | 25.0 g |
| Water to 1 L solution | |
| pH adjusted to 10.12 with KOH | | and wherein R is a substituted or unsubstituted alkyl, aryl or heterocyclic group bonded to N by a carbon atom.

In one embodiment the hydroxylamine compound is represented by Formula III or IV:

wherein X, $X^1$ and $X^2$ are solubilizing groups;
$R^1$, $R^2$, $R^3$, $R^4$, $R^5$ and R6 are independently substituent groups;
m, n and r are independently 0 to 4;
o, p and q are independently 0 to 2; and
$R^7$ is a substituted or unsubstituted alkyl, aryl or heterocyclic group. This invention further provides novel antioxidants represented by Formula IV.

It has been found that many hydroxylamines lower the pH of a developer solution as they degrade. Lowering the pH of the developer results in a decrease in developer activity. The hydroxylamine compounds of this invention have little effect on the pH of developer. The compounds of this invention are mono and disubstituted hydroxylamines that have substituents that stabilize the product of antioxidant oxidation, namely, the nitrone. They further contain solubilizing substituents to effect easy dissolution in aqueous media. Many of the compounds of this invention may be synthesized in a simple one step procedure. When used in a color developer they are strong antioxidants which are odor free.

DETAILED DESCRIPTION OF THE INVENTION

In one embodiment the hydroxylamine compounds of this invention are represented by Formula I or II:

I

II wherein Stab is independently a stabilizing group such that when the hydroxylamine compound is added to a test developer solution of the following formula the pH of the test developer solution decreases less than 0.12 at an aeration time of 90 hours.

| Components | Quantity/L |
|---|---|
| Lithium salt of sulfonated Polystyrene (30% wt/wt Liq) | 0.25 mL |
| Triethanolamine | 11.0 mL |
| Stilbene Stain-Reducing Agent | 2.3 g |
| Hydroxylamine compound | 0.05 moles |
| Lithium Sulfate | 2.7 g |
| 1-Hydroxyethylidene-1-diphosphonic acid (60% wt/wt Liq) | 0.8 mL |
| Potassium Chloride | 1.8 g |
| Potassium Bromide | 0.2 g |
| 4-amino-3-methyl-N-ethyl-N-(β-methanesulfonamidoethyl)aniline (color developer) | 4.85 g |
| Potassium Carbonate | 25.0 g |
| Water to 1 L solution | |
| pH adjusted to 10.12 with KOH | |

The aeration is performed at ambient temperature by areating the developer solution with air (21% $O_2$/79% $N_2$) for a length of time, making periodic pH and color developer concentration measurements. The containers used for the developer solutions are one liter graduated cylinders thereby allowing for the accurate replacement of evaporated water before each pH and color developer concentration measurement.

R is a substituted or unsubstituted alkyl, aryl or heterocyclic group. This definition of R also includes combinations of these groups. The R group is directly bonded to N through a carbon atom. Preferably, the alkyl group contains 1 to 20 carbon atoms, with 1 to 10 carbon atoms being most preferred, and the aryl group contains 6 to 10 carbon atoms, with 6 carbon atoms being most preferred. The heterocyclic group may be a 5 to 15-membered ring containing one or two heteroatoms. Preferred hetero atoms are nitrogen, sulfur and oxygen. More preferably, the heterocyclic group is a 5 or 6-membered ring. Examples of suitable aryl groups include phenyl, tolyl, naphthyl, and cycloheptatrienyl. Examples of suitable heterocyclic rings are pyrrole, furan, tetrahydrofuran, thiofuran, pyridine, picoline, piperidine, morpholine, pyrrolidine, thiophene, oxazole, thiazole, imidazole, triazole, tetrazole and oxadiazole. Preferably, R is a straight or branched alkyl group having 1 to 6 carbon atoms which may be substituted with a solubilizing group. Some examples of suitable groups are methyl, ethyl, isopropyl, t-butyl, —(CH$_2$)—COOR$^8$, —CH$_2$CH$_2$OH, and —CH$_2$COOR$^8$ wherein R$^8$ is H or an alkali or alkaline earth metal. R may also preferably be a substituted or unsubstitued phenyl group.

Other substituents of R may include, for example, alkyl groups (for example, methyl, ethyl, hexyl), fluoroalkyl groups (for example, trifluoromethyl), aryl groups (for example, phenyl, naphthyl, tolyl), aryloxy groups (for example, phenoxy), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, alkoxy groups (for example, methoxy, ethoxy, octyloxy), hydroxy groups, halogen atoms, alkylthio groups, arylthio groups, acyl groups and amino groups.

In addition to stabilizing the pH, the Stab groups must be soluble enough to effect dissolution in aqueous buffered alkaline solutions. They must also be compatible with a photographic developing composition and must have no unacceptably deleterious effects on the photographic processing system or the photographic element being processed.

It is believed, although the inventors are not limited to the theory, that the Stab groups of this invention act through the following mechanism. An intermediate product of hydroxylamine oxidation is a nitrone, of the formula:

Such nitrones are susceptible to degradation, particularly hydrolysis, (see Tae-Rin Kim and Kwang-II Lee, Bull. Korean Chem. Soc., vol. 12, #3, p. 273 (1991)) which ultimately acidifies the solution. Thus, the pH of a developer solution can be lowered as a result of nitrone degradation. If the nitrone function is stabilized the change in developer pH can be minimized. Therefore it is believed that Stab should be a group that stabilizes the nitrone against degradation, particularly hydrolysis. Possible stabilizing groups include isopropyl, benzyl, t-butyl and R'CHCOOR", wherein R' is H, or an alkyl group and R" is H or an alkali metal ion.

Regardless of the above test and theory, in another embodiment, and preferably, the hydroxylamine compounds of this invention are represented by Formula III or IV, with Formula III being more preferred.

wherein X, X$^1$ and X$^2$ are solubilizing groups;

R$^1$, R$^2$, R$^3$, R$^4$, R$^5$ and R6 are independently substituent groups;

m, n and r are independently 0 to 4;

o, p and q are independently 0 to 2; and $R^7$ is a substituted or unsubstituted alkyl, aryl or heterocyclic group.

X, $X^1$ and $X^2$ may be any solubilizing group which reduces the vapor pressure of the hydroxylamine compound enough to render the compound free of significant unpleasant odor and which is not deleterious to the developing composition. Preferably, X, $X^1$ $X^2$ are independently —$CH_2OH$, —$SO_3M$, —$PO_3M$ or —COOM, and most preferably they are —COOM. M is —H or an organic or inorganic cationic group. Preferably M is —H or an alkali metal ion. If M is an alkali metal ion, sodium or potassium are preferred.

$R^1$, $R^2$, $R^3$, $R^4$, $R^5$ and $R^6$ may be any substituent groups which do not interfere with the stabilizing effect of the benzyl group or the solubilizing effect of the solubilizing groups. Such substituents must also be compatible with the developer composition and must not negatively impact the photographic processing system. Such substituents may include, for example, alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups. Preferably $R^2$, $R^3$ and $R^5$ are H or a substituted or unsubstituted aryl or alkyl group, and more preferably a substituted or unsubstituted phenyl Group or alkyl group of 1 to 6 carbon atoms. The substituent may be a solubilizing group. Most preferably $R^2$, $R^3$ and $R^5$ are isopropyl, benzyl, t-butyl and $CH_2COOR^8$, wherein $R^8$ is H or an alkali or alkaline earth metal. $R^7$ is the same as R described above.

In the more preferred embodiments of the hydroxylamine compounds, m, n, o, and p are 0. The most preferred compounds are N-methyl-N-(p-carboxybenzyl) hydroxylamine, N-isopropyl-N-(p-carboxybenzyl) hydroxylamine, N, N-bis (p-carboxybenzyl)hydroxylamine, N, N,-bis (4-hydroxymethylbenzyl)hydroxylamine, N-(4-hydroxymethylbenzyl)-N-isopropylhydroxylamine and N-(4-hydroxymethylbenzyl)-N-methylhydroxylamine.

The above mentioned compounds of the present invention can be prepared by reacting di-substituted or mono-substituted hydroxylamines with α-halo-toluic acids. These reactions yield substituted hydroxylamines with benzylic acid substituents.

The hydroxylamine compounds of this invention may be dissolved in an aqueous solution and then added to the developing composition or they may be added directly to the composition. The useful concentration of the compounds is about 0.005M to 0.1M, with 0.025M to 0.05M being preferred. The useful pH range of the developer is 9 to 13, with 9 to 11 being more preferred and 9.9 to 10.2 being most preferred.

The color developing composition must contain a primary aromatic amino color developing agent. These color developing agents are well known and widely used in variety of color photographic processes. They include aminophenols and p-phenylenediamines.

Examples of aminophenol developing agents include o-aminophenol, p-aminophenol, 5-amino-2-hydroxytoluene, 2-amino-3-hydroxytoluene, 2-hydroxy-3-amino-1,4-dimethylbenzene, and the like.

Particularly useful primary aromatic amino color developing agents are the p-phenylenediamines and especially the N-N-dialkyl-p-phenylenediamines in which the alkyl groups or the aromatic nucleus can be substituted or unsubstituted. Examples of useful p-phenylenediamine color developing agents include: N-N-diethyl-p-phenylenediamine monohydrochloride, 4-N,N-diethyl-2-methylphenylenediamine monohydrochloride, 4-(N-ethyl-N-2-methanesulfonylaminoethyl)-2-methylphenylenediamine sesquisulfate monohydrate, and 4-(N-ethyl-N-2-hydroxyethyl)-2-methylphenylenediamine sulfate.

The color developer solution can also contain chemical agents that sequester metal ions, such as the chelates described by the following formulas;

C1

C2

C3

C4

C5

C6

C7

C8

C9

C10

-continued

| | | |
|---|---|---|
| HOOC—CH₂\\N—CH—CH₂—CH₂—N/CH₂COOH<br>HOOC—CH₂/   \|           \\CH₂COOH<br>              CH₃ | C11 | HOOC—CH₂\\N—CH—CH₂—CH—N/CH₂COOH<br>HOOC—CH₂/   \|           \|      \\CH₂COOH<br>              CH₃         CH₃ | C12 |
| HOOC—CH₂\\  CH₃   CH₃ /CH₂COOH<br>HOOC—CH₂/N—C—CH₂—CH—N\\CH₂COOH<br>              \|<br>              CH₃ | C13 | $-(NCH_2CH_2NCH_2CH_2NCH_2CH_2NCH_2CH_2NCH_2CH_2)_x-$ with CH₂PO₃Na₂, CH₂PO₃Na₂, OH, CH₂PO₃Na₂ substituents | C14 |
| NaO₃SCH₂CH₂CH₂PO₃Na₂ | C15 | $-(NCH_2CH_2NCH_2CH_2NCH_2CH_2NCH_2CHCH_2)_x-$ with CH₂PO₃Na₂, CH₂PO₃Na₂, OH, CH₂PO₃Na₂ substituents | C16 |
| NH₂(CH₂)₅C(PO₃H₂)(PO₃H₂)OH | C17 | H₂O₃PCH₂CHCH₂PO₃H₂ with PO₃H₂ substituent | C18 |
| $-(NCH_2CH_2NCH_2CH_2NCH_2CH_2NCH_2CHCH_2)_x-$ with CH₂PO₃Na₂ substituents and OH | C19 | H₂O₃PCH₂CHCH₂PO₃H₂ with PO₃H₂ and PO₃H₂ substituents | C20 |
| CH₃—C(PO₃H₂)(PO₃H₂)—N=C(NH₂)(CH₃) | C21 | $-(NCH_2CH_2NCH_2CH_2NCH_2CH_2NCH_2CHCH_2)_x-$ with CH₂PO₃Na₂ groups and OH | C22 |
| $-(CH_2-C(OH)(COONa))_x-$ | C23 | NaOOCCH₂NH—CHOONa<br>                      \|<br>                      HOCHOONa | C24 |
| P[CH₂N(CH₂COONa)₂]₃·H₂O | C25 | P[CH₂N(CH₂COONa)₂]₃·H₂O | C26 |
| CH₃CH₂O—C(COONa)(COONa)—OCH₂COONa | C27 | CH₃—C(PO₃H₂)(PO₃H₂)—N=C(CH₃)(CH₃) | C28 |
| HOOCH₂C\\N—CH₂CH₂—N/CH₂COOH<br>    H₂C                 CH₂<br>     \|                    \|<br>     ⌬                  ⌬—OH<br>HOOCH₂C          CH₂COOH | C29 | (18-crown-6 structure with 6 oxygens) | C30 |
| (15-crown-5 structure with 5 oxygens) | C31 | CH₃CNHCCH₃ with PO₃HNa, O, PO₃H₂ substituents | C32 |
| (HO)₂P(=O)CH₂CHCOOH<br>              \|<br>              NHCH₂COOH | C33 | H₂O₃P—CH₂CHCOOH<br>              \|<br>              NHCH₂COOH | C34 |
| HOOCCHCHCOOH with PO₃H₂ and PO₃H₂ | C35 | H₂O₃P—CHCOOH<br>         \|<br>         CH₂COOH | C36 |

-continued

C37

C38

C40

C39

C42

C41

C44

C43

C46

C45

C48

C47

C50

NaOOCH$_2$NHCHCOONa     C49
|
HOCHCOONa

Also contained in the color developing composition are alkali metal halides, such as potassium and/or sodium chloride, potassium and/or sodium bromide, and potassium and/or sodium iodide. The color developing composition may also contain anti-oxidants, anti-foggants, solubilizing agents, brightening agents, and so forth.

In order to maintain the pH of the solution, buffers are added in a concentration range of 0.005M to 0.5M. Examples of buffers that are suitable for the present invention include carbonates, phosphates, and borates.

The color developing compositions may be utilized in the various processing systems known in the art. They may be particularly useful with Low Volume Thin Tank processing systems. A Low Volume Thin Tank processor provides a small volume for holding processing solution. As a part of limiting the volume of the processing solution, a narrow processing channel is provided. The processing channel, for a processor used for photographic paper, should have a thickness equal to or less than about 50 times the thickness of paper being processed, preferably a thickness equal to or less than about 10 times the paper thickness. In a processor for processing photographic film, the thickness of the processing channel should be equal to or less than about 100 times the thickness of photosensitive film, preferably, equal to or less than about 18 times the thickness of the photographic film. An example of a low volume thin tank processor which processes paper having a thickness of about 0.008 inches would have a channel thickness of about 0.080 inches and a processor which process film having a thickness of about 0.0055 inches would have a channel thickness of about 0.10 inches.

The total volume of the processing solution within the processing channel and recirculation system is relatively smaller as compared to prior art processors. In particular, the total amount of processing solution in the entire processing system for a particular module is such that the total volume in the processing channel is at least 40 percent of the total volume of processing solution in the system. Preferably, the volume of the processing channel is at least about 50 percent of the total volume of the processing solution in the system.

In order to provide efficient flow of the processing solution through the opening or nozzles into the processing channel, it is desirable that the nozzles/opening that deliver the processing solution to the processing channel have a configuration in accordance with the following relationship:

$$1 \leq F/A \leq 40$$

wherein:

F is the flow rate of the solution through the nozzle in gallons per minute; and A is the cross-sectional area of the nozzle provided in square inches.

Providing a nozzle in accordance with the foregoing relationship assures appropriate discharge of the processing solution against the photosensitive material. Such Low Volume Thin Tank systems are described in more detail in

| Title | Pub. No. or Appln. No | Pub. Date |
|---|---|---|
| PROCESS RACK INTEGRAL WITH PUMPS | US 5,294,956 | 15MAR94 |
| A DRIVING MECHANISM FOR A PHOTOGRAPHIC PROCESSING APPARATUS | EP 559,027 | 08SEP93 |
| ANTI-WEB ADHERING CONTOUR SURFACE FOR A PHOTOGRAPHIC PROCESSING APPARATUS | US 5,179,404 | 12JAN93 |
| A RACK AND A TANK FOR A PHOTOGRAPHIC PROCESSING APPARATUS | EP 559,025 | 08SEP93 |
| A SLOT IMPINGEMENT FOR A PHOTOGRAPHIC PROCESSING APPARATUS | US 5,270,762 | 14DEC93 |
| RECIRCULATION, REPLENISHMENT, REFRESH, RECHARGE AND BACKFLUSH FOR A PHOTOGRAPHIC PROCESSING APPARATUS | EP 559,026 | 08SEP93 |
| PHOTOGRAPHIC PROCESSING APPARATUS | WO 92/10790 | 25JUN92 |
| PHOTOGRAPHIC PROCESSING APPARATUS | WO 92/17819 | 15OCT92 |
| PORTABLE FILM PROCESSING UNIT | WO 93/04404 | 03MAR93 |
| CLOSURE ELEMENT | WO 92/17370 | 15OCT92 |
| PHOTOGRAPHIC PROCESSING TANK | WO 91/19226 | 12DEC91 |
| METHOD AND APPARATUS FOR PHOTOGRAPHIC PROCESSING | WO 91/12567 | 22AUG91 |
| PHOTOGRAPHIC PROCESSING APPARATUS | WO 92/07302 | 30APR92 |
| PHOTOGRAPHIC PROCESSING APPARATUS | WO 93/00612 | 07JAN93 |
| PHOTOGRAPHIC PROCESSING APPARATUS | WO 92/07301 | 30APR92 |
| PHOTOGRAPHIC PROCESSING APPARATUS | WO 92/09932 | 11JUN92 |

Typically, silver halide photographic elements are bleached and fixed after development. Bleaching agents which may be used include compounds of polyvalent metal such as iron (III), cobalt (III), chromium (VI), and copper (II), peracids, quinones, and nitro compounds. Typical bleaching agents are iron (III) salts, such as ferric chloride, ferricyanides, bichromates, and organic complexes of iron (III) and cobalt (III). Ferric complexes of aminopolycarboxylic acids and persulfate are most commonly used as bleaching agents with ferric complexes of aminopolycarboxylic acids being preferred. Some examples of useful ferric complexes include complexes of:
nitrilotriacetic acid,
ethylenediaminetetraacetic acid,
propylenediamine tetraacetic acid,
diethylenetriamine pentaacetic acid,
ortho-diamine cyclohexane tetraacetic acid,
ethylene glycol bis(aminoethyl ether)tetraacetic acid,
diaminopropanol tetraacetic acid,
N-(2-hydroxyethyl)ethylenediamine triacetic acid,
ethyliminodipropionic acid,
methyliminodiacetic acid,
ethyliminodiacetic acid,
cyclohexanediaminetetraacetic acid,
glycol ether diamine tetraacetic acid.

Preferred aminopolycarboxylic acids include 1,3-propylenediamine tetraacetic acid, methyliminodiactic acid and ethylenediamine tetraacetic acid. The bleaching agents may be used alone or in a mixture of two or more; with useful amounts typically being at least 0.1 moles per liter of bleaching solution, with at least 0.5 moles per liter of bleaching solution being preferred.

In addition, water-soluble aliphatic carboxylic acids such as acetic acid, citric acid, propionic acid, hydroxyacetic acid, butyric acid, malonic acid, succinic acid and the like may be utilized in any effective amount. Useful amounts are typically at least 0.35 moles per liter of bleaching solution, with at least 0.7 moles being preferred and at least 0.9 moles being most preferred.

These ferric aminopolycarboxylate complexes are used in the form of salts, for example as sodium, potassium, or ammonium salts. The bleaching solutions may contain other addenda known in the art to be useful in bleaching compositions, such as sequestering agents, sulfites, non-chelated salts of aminopolycarboxylic acids, bleaching accelerators, re-halogenating agents, anti-calcium agents, and/or anti-phosphate agents. The bleaching solution is generally used at a pH of 0.45 to 9.0, more preferably 4.0 to 6.8, and most preferably 4.0 to 5.5.

Examples of fixing agents which may be used are water-soluble solvents for silver halide such as: a thiosulfate (e.g., sodium thiosulfate and ammonium thiosulfate); a thiocyanate (e.g., sodium thiocyanate and ammonium thiocyanate); a thioether compound (e.g., ethylenebisthioglycolic acid and 3,6-dithia-1,8-octanediol); or a thiourea. These fixing agents can be used singly or in combination. Thiosulfate is preferably used in the present invention.

The concentration of the fixing agent per liter is preferably about 0.2 to 2 mol. The pH range of the fixing solution is preferably 3 to 10 and more preferably 5 to 9. In order to adjust the pH of the fixing solution an acid or a base may be added, such as hydrochloric acid, sulfuric acid, nitric acid, acetic acid, bicarbonate, ammonia, potassium hydroxide, sodium hydroxide, sodium carbonate or potassium carbonate.

The fixing solution may also contain a preservative such as a sulfite (e.g., sodium sulfite, potassium sulfite, and ammonium sulfite), a bisulfite (e.g., ammonium bisulfite, sodium bisulfite, and potassium bisulfite), and a metabisulfite potassium metabisulfite, sodium metabisulfite, and ammonium metabisulfite). The content of these compounds is about 0 to 0.50 mol/liter, and more preferably 0.02 to 0.40 mol/liter as an amount of sulfite ion. Ascorbic acid, a carbonyl bisulfite acid adduct, or a carbonyl compound may also be used as a preservative.

A stabilizer bath is commonly employed for final washing and hardening of the bleached and fixed photographic element prior to drying. Alternatively, a final rinse may be used. A bath can be employed prior to color development, such as a prehardening bath, or the washing step may follow the stabilizing step. Other additional washing steps may be utilized. Additionally, reversal processes which have the additional steps of black and white development, chemical fogging bath, light re-exposure, and washing before the color development are contemplated. In reversal processing there is often a bath which precedes the bleach which may serve many functions, such as an accelerating bath, a clearing bath or a stabilizing bath. Conventional techniques for processing are illustrated by Research Disclosure, Paragraph XIX.

The photographic elements useful with this invention can be single color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in Whitmore U.S. Pat. No. 4,362,806 issued Dec. 7, 1982. The element can contain additional layers such as filter layers, interlayers, overcoat layers, subbing layers and the like. The element may also contain a magnetic backing such as described in No. 34390, *Research Disclosure*, November, 1992.

In the following discussion of suitable materials for use in the emulsions and elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, the disclosures of which are incorporated herein by reference. This publication will be identified hereafter by the term "Research Disclosure".

The silver halide emulsions employed in the elements of this invention can be either negative-working or positive-working. Examples of suitable emulsions and their preparation are described in Research Disclosure Sections I and II and the publications cited therein. Other suitable emulsions are (111) tabular silver chloride emulsions such as described in U.S. Pat. Nos. 5,176,991 (Jones et al); 5,176,992 (Maskasky et al); 5,178,997 (Maskasky); 5,178,998 (Maskasky et al); 5,183,732 (Maskasky); and 5,185,239 (Maskasky) and (100) tabular silver chloride emulsions such as described in EPO 534,395, published Mar. 31, 1993 (Brust et al). Some of the suitable vehicles for the emulsion layers and other layers of elements of this invention are described in Research Disclosure Section IX and the publications cited therein.

The silver halide emulsions can be chemically and spectrally sensitized in a variety of ways, examples of which are described in Sections III and IV of the Research Disclosure. The elements of the invention can include various couplers including, but not limited to, those described in Research Disclosure Section VII, paragraphs D, E, F, and G and the publications cited therein. These couplers can be incorporated in the elements and emulsions as described in Research Disclosure Section VII, paragraph C and the publications cited therein.

The photographic elements of this invention or individual layers thereof can contain among other things brighteners (examples in Research Disclosure Section. V), antifoggants and stabilizers (examples in Research Disclosure Section VI), antistain agents and image dye stabilizers (examples in Research Disclosure Section VII, paragraphs I and J), light absorbing and scattering materials (examples in Research Disclosure Section VIII), hardeners (examples in Research Disclosure Section X), plasticizers and lubricants (examples in Research Disclosure Section XII), antistatic agents (examples in Research Disclosure Section XIII), matting agents (examples in Research Disclosure Section XVI) and development modifiers (examples in Research Disclosure Section XXI).

The photographic elements can be coated on a variety of supports including, but not limited to, those described in Research Disclosure Section XVII and the references described therein.

Photographic elements can be exposed to actinic radiation, typically in the visible region of the spectrum, to form a latent image as described in Research Disclosure Section XVIII and then processed to form a visible dye image, examples of which are described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide, the processing step described above gives a negative image. To obtain a positive (or reversal) image, this step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

The following examples are intended to illustrate, but not limit, the invention.

EXAMPLES

Example 1

Preparation of N,N-bis(p-carboxybenzyl)hydroxylamine (BCH).

A filtered solution of 4-(chloromethyl)benzoic acid (33.0 g, 186 mmol) and NaOH (7.43 g, 186 mmol) was added over a 5 minute period to a solution of hydroxylamine hydrochloride (6.45 g, 92.8 mmol), NaOH (3.7 g, 92.8 mmol) and water (100 mL). The solution was stirred mechanically, and heated to 45° C. The pH of the solution was kept at 8–10 by the addition of aqueous NaOH. When the pH of the solution stopped decreasing, the solution was filtered, then acidified with concentrated $H_2SO_4$ to a pH of 4. The resulting white solid was isolated by filtration and washed with copious amounts of water until no cloudiness was observed when the filtrate was treated with aqueous silver nitrate. The product was dried in vacuo then dissolved in boiling N,N-dimethylformamide (DMF) (60 mL) and the hot solution treated with water until slightly turbid. The solution was cooled and the white solid which formed was isolated by filtration, washed with water, and dried in vacuo at 70° C. at 0.01 Torr to give 10.9 g (39%) product. The product met the following criteria: $^1H$ NMR (DMSO-$d_6$) δ 12.87 (br, s, 2H), 7.86 (d, J=7.5 Hz, 4H), 7.45 (d, J=7.5 Hz, 4H), 3.87 (s, 4H). $^{13}C$ {$^1H$} NMR (DMSO-$d_6$) δ 167.3, 143.6, 129.4, 129.1, 129.0, 63.5. Analyzed for $C_{16}H_{15}NO_5$: C, 63.78; H, 5.02; N, 4.65. Found: C, 63.62; H, 5.11; N, 4.84.

Example 2

Alternative Preparation of N,N-bis (p-carboxybenzyl) hydroxylamine (BCH).

preparation of N,N-bis-(p-methoxycarbonylbenzyl) hydroxylamine:

Method A: (from benzyl chloride)

A solution of 10.0 g (0.054 moles) of p-methoxycarbonylbenzyl chloride in 60 mL of dry DMF was added dropwise at room temperature under a nitrogen atmosphere to a stirred suspension of 1.87 g (0.027 moles) of hydroxylamine hydrochloride and 11.4 g (0.108 moles) of freshly ground anhydrous sodium carbonate in 50 mL of dry (3A molecular sieves) N,N-dimethylformamide (DMF). After the addition was complete, the flask was put into a 70° C. oil bath and stirred until all of the starting material was consumed, approximately 24 hours (determined by TLC using 4:1 (hexanes:ethyl acetate) as eluent). The slurry was filtered hot to remove the insoluble material, and the filter cake was rinsed with some more DMF. The filtrate was concentrated under reduced pressure to a viscous colorless oil and 100 mL of a 1:1 EtOH:$H_2O$ mixture was added slowly to the oil and swirled around. A white solid crystallized out of solution and, after standing for a few minutes, it was collected and washed with some more 1:1 EtOH:$H_2O$ and allowed to dry on the filter funnel. It was dried in the vacuum overnight to give 7.4 g (0.0225 moles) of a fluffy white solid (83% yield). mp 129°–130° C.; $^1$H NMR (DMSO-d6) δ 7.925 (s,1H); δ 7.90 (d,4H); δ 7.475 (d,4H); δ 3.9 (s,4H); δ 3.8 (s,6H).

Analysis: Calcd for $C_{18}H_{19}NO_5$: C, 65.6; H, 5.8; N, 4.3. Found: C, 65.52; H, 5.73; N, 4.17.

Method B: (from benzyl bromide)

A solution of 22.47 g (0.098 moles) of p-methoxycarbonylbenzyl bromide in 90 mL of dry DMF was added dropwise at room temperature under a nitrogen atmosphere to a stirred suspension of 3.33 g (0.048 moles) of hydroxylamine hydrochloride and 20.34 g (0.192 moles) of anhydrous sodium carbonate in 60 mL of dry (DMF). The mixture was stirred for 24 hours and TLC (4:1 (hexanes:ethyl acetate)) showed that all of the starting material had reacted. The reaction mixture was filtered, the solid was washed with DMF, and the filtrate was concentrated under reduced pressure to a viscous yellow oil and swirled around. A fluffy white precipitate formed. The solid was collected and washed with some ethanol:water and then dried in the vacuum oven to give 11.7 g (0.036 moles) of solid white (75% yield) that melts at 129°–130° C.

Hydrolysis of the ester to N,N-bis(p-carboxybenzyl) hydroxylamine:

A solution of 6.0 mL of 5N NaOH (0.03 moles) in 100 mL of water was added dropwise at room temperature under nitrogen to 5.0 g (0.015 moles) of N, N-bis(p-methoxycarbonylbenzyl)-hydroxylamine dissolved in 150 mL of methanol. After the addition was complete, the flask was put into a 60° C. oil bath and stirred overnight. It was cooled to room temperature and was acidified to pH 5.2 with conc. HCl; a white solid precipitated out of solution. It was cooled in an ice bath and the solid was collected, washed well with water and then ethyl ether, and dried in the vacuum oven to give 3.8 g of the product. A second crop was obtained from the filtrate to give a total of 4.2 g of the above-named product (92% yield). mp 252° C. (dec); $^1$H NMR (DMSO-d6) δ 12.8 (br.s.,2H); δ 7.9 (br.d.,5H); δ 7.4 (d,4H); δ 3.9 (s,4H).

Analysis: Calcd for $C_{16}H_{15}NO_5$: C, 63.78; H, 5.02; N, 4.65. Found: C, 63.35; H, 5.04; N, 4.59.

Example 3

Preparation of N-isopropyl-N-(4-carboxybenzyl) hydroxylamine

N-isopropyl-N-(4-carbomethoxybenzyl)hydroxylamine

N-isopropylhydroxylamine (13.74 g, 90%, 165 mmol), 4-carbomethoxybenzyl chloride (30.4 g, 165 mmol) and $Na_2CO_3$ (18.0 g, 170 mmol) were dissolved in DMF (150 mL) and stirred at 60° C. under Argon for 20 h. The reaction mixture was filtered, concentrated, diluted with $CHCl_3$ (300 mL), washed with water (3×200 mL), dried with $MgSO_4$, concentrated, dissolved in EtOAC (10 mL) and chromatographed on an Si gel eluting with 4:1 hexanes/EtOAc to give 15.2 g (41%) N-isopropyl-N-(4-carbomethoxybenzyl)-hydroxylamine. $^1$H NMR (DMSO-d6) δ 7.85 (d, J=8.2 Hz, 2), 7.43 (d, J=8.2 Hz, 2), 7.44 (s, 1), 3.80 (s, 3), 3.73 (s, 1), 2.85 (sept, J=6.3 Hz, 1), 1.02 (d, J=6.3 Hz, 6). $^{13}$C{1H} NMR (DMSO-$d_6$) δ 166.2, 145.6, 129.0, 128.8, 127.8, 59.3, 56.8, 52.0, 18.4.

A MeOH solution (75 mL) of N-isopropyl-N-(4-carbomethoxybenzyl)-hydroxylamine (13.2 g, 59.1 mmol) was heated to 60° C. and treated with NaOH (2.46 g, 61.5 mol) in water 50 (mL). The reaction was allowed to stir for 18 h under argon and was then filtered, concentrated to remove most of the MeOH, diluted with water (100 mL), an acidified to pH-4.5 with conc $H_2SO_4$. The white solid was stirred at ambient temperature for 3 h, isolated by filtration, washed with copious amounts of water and then dried in vacuo at 60° C. to give 10.34 g (83%) N-isopropyl-N-(4-carboxybenzyl)hydroxylamine. mp 201°–202° C.(dec). $^1$H NMR (DMSO-d6) δ 12.6 (br, 1), 7.83 (d, J=8.1 Hz, 2), 7.49 (s, 1), 7.41 (d, J=8.1 Hz, 2), 3.72 (s, 2), 2.85 (sept, J=6.4 Hz, 1), 1.02 (d, J=6.4 Hz, 6).

Analysis: Calcd for $C_{11}H_{15}NO_3$: C, 63.14; H, 7.23; N, 6.69. Found: C, 63.00; H, 6.91;.N, 6.38.

Example 4

Preparation of N-methyl-N-(4-carbomethoxybenzyl) hydroxylamine (HBC)

A neutralized (85.0 g NaOH, 2.1 mol) solution of methylhydroxylamine hydrochloride (176.0 g, 2.1 mol) in water (700 mL) was added to a solution of methyl-4-formylbenzoate (MFB)(328.3 g, 2.0 mol) in methanol (800 mL) at 50°–60° C. The solution was stirred for 1 h at 50°–60° C. then the heat was removed and the solution was stirred for an additional 17 h. After this tirade the contents of the vessel were concentrated to remove most of the methanol, and the white solid which formed was isolated by filtration. This was nitrone Intermediate 1. After water washing and drying the yield of nitrone Intermediate 1 was 273.2 g (71%). mp 117°–118.5° C. $^1$H NMR (CDCl$_3$) δ8.21 (d,J=8.4 Hz, 2), 8.07 (d,J=8.4 Hz, 2), 7.41 (s, 1), 3.87 (s, 3), 3.86 (s, 3). Anal. calc'd for C$_{10}$H$_{11}$NO$_3$: C, 62.17; H, 5.74; N, 7.25. Found C, 61.71; H, 5.57; N, 7.17.

An aqueous solution (500 mL) of KBH$_4$(52.5 g, 973 mmol) was added in one portion to a warm (50° C.) solution of nitrone Intermediate 1 (62.7 g, 324 mmol) in methanol (600 mL) and stirred for 25 min. The reaction was then cooled in an ice bath and acidified to pH=6.2 with concentrated HCl. The reaction mixture was concentrated to remove methanol, diluted with water (300 mL) and extracted with CHCl$_3$ (3×300 mL). The combined extracts were washed with water (1×300 mL), dried (MgSO$_4$) and concentrated to give 49.7 g of a hydroxylamine ester, Intermediate 2 (79%) as a white solid. mp 87°–89° C. $^1$H NMR (CDCl$_3$) δ8.06 (s, 1), 7.91 (d,J=7.8 Hz, 2), 7.31 (d,J=7.8 Hz, 2), 3.83 (s, 3), 3.70 (s, 2), 2.48 (s, 3). $^{13}$C NMR (CDCl$_3$) δ166.7, 141.7, 129.6, 129.4, 129.2, 65.6, 5.9, 47.6. Anal. calc'd for C$_{10}$H$_{13}$NO$_3$: C, 61.53; H, 6.71; N, 7.17. Found C, 61.24; H, 6.63; N, 7.23.

A warmed (60° C.) methanolic solution (125 mL) of the hydroxylamine ester Intermediate 2 (53.8 g, 276 mmol) was treated with aqueous NaOH (11.46 g, 287 mmol in 250 mL water) and allowed to stir under an inert atmosphere for 22 h at that temperature. The heat was removed and the solution was made acidic (pH=5.5) with conc H2SO04. The white solid which precipitated was isolated by filtration and washed extensively with water to afford 41.75 g (84%) of the final product, N-methyl-N-(4-carbomethoxybenzyl) hydroxylamine (HBC), as a white solid. mp 196°–197° C. (dec). $^1$H NMR (DMSO-d$_6$) δ7.85 (br s, 1), 7.83 (d,J=8.0 Hz, 2), 7.37 (d,J=8.0 Hz, 2), 3.68 (s, 2), 2.49 (s, 3). $^{13}$C NMR (DMSO-d$_6$) δ167.3, 143.8, 129.3, 129.1, 129.0, 65.2, 48.6. Anal. calc'd for C$_9$H$_{11}$NO$_3$: C, 59.66; H, 6.12; N, 7.73. Found C, 59.58; H, 6.03; N, 7.70.

Carboxylic (COOH) or sulfonic acid esters (SO$_3$R) may also be employed in this invention instead of the free acids. At the high pH present in the developing medium, the ester groups will be hydrolyzed to the carboxylate or sulfonate salts respectively groups may be alkyl (C1–C18), aryl (C6–C10) or substituted aryl, benzyl or alkaryl.

Example 5

Developer solutions as described in Table 1 containing the hydroxylamine compounds listed in Table 2 were prepared.

TABLE 1

| Developer Formulation | |
|---|---|
| Components | Quantity/L |
| Lithium salt of sulfonated Polystyrene (30% wt/wt Liq) | 0.25 mL |
| Triethanolamine | 11.0 mL |
| Stilbene Stain-Reducing Agent | 2.3 g |
| Hydroxylamine Anti-oxidant | 0.05 moles |
| Lithium Sulfate | 2.7 g |
| 1-Hydroxyethylidene-1-diphosphonic acid (60% wt/wt Liq) | 0.8 mL |
| Potassium Chloride | 1.8 g |
| Potassium Bromide | 0.2 g |
| 4-amino-3-methyl-N-ethyl-N-(β-methanesulfonamidoethyl)aniline (color developer) | 4.85 g |

TABLE 1-continued

| Developer Formulation | |
|---|---|
| Components | Quantity/L |
| Potassium Carbonate | 25.0 g |
| Water to 1 L solution | |
| pH adjusted to 10.12 with KOH | |

TABLE 2

| Hydroxylamine Anti-oxidant | |
|---|---|
| N,N-Bis(p-carboxybenzyl)hydroxylamine (BCH) | Invention |
| N,N-Diethylhydroxylamine (DEH) | Comparative Example |
| N,N-Bis(2-ethylpyridine)hydroxylamine (BPH) | Comparative Example |
| N-Methyl-N-p-carboxybenzylhydrozylamine (HBC) | Invention |
| N,N-Diacetic aicd hydroxylamine (HIDA) | Comparative Example |

Figure 1:
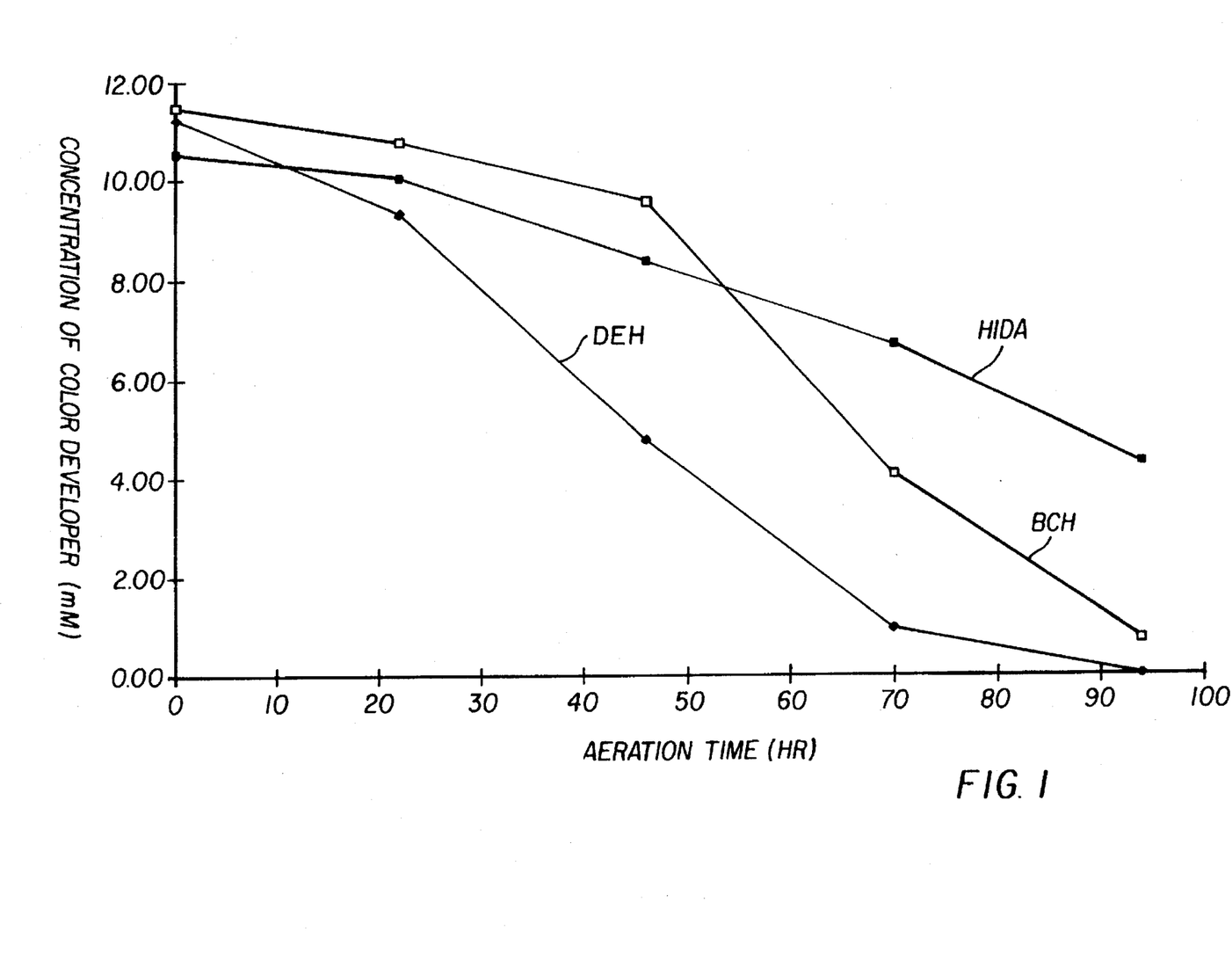
FIG. 1 depicts the effect over time that three different hydroxylamine antioxidants, HIDA, BCH, and DEH, have on the concentration of color developer contained in an aerated developer solution.
Figure 2:
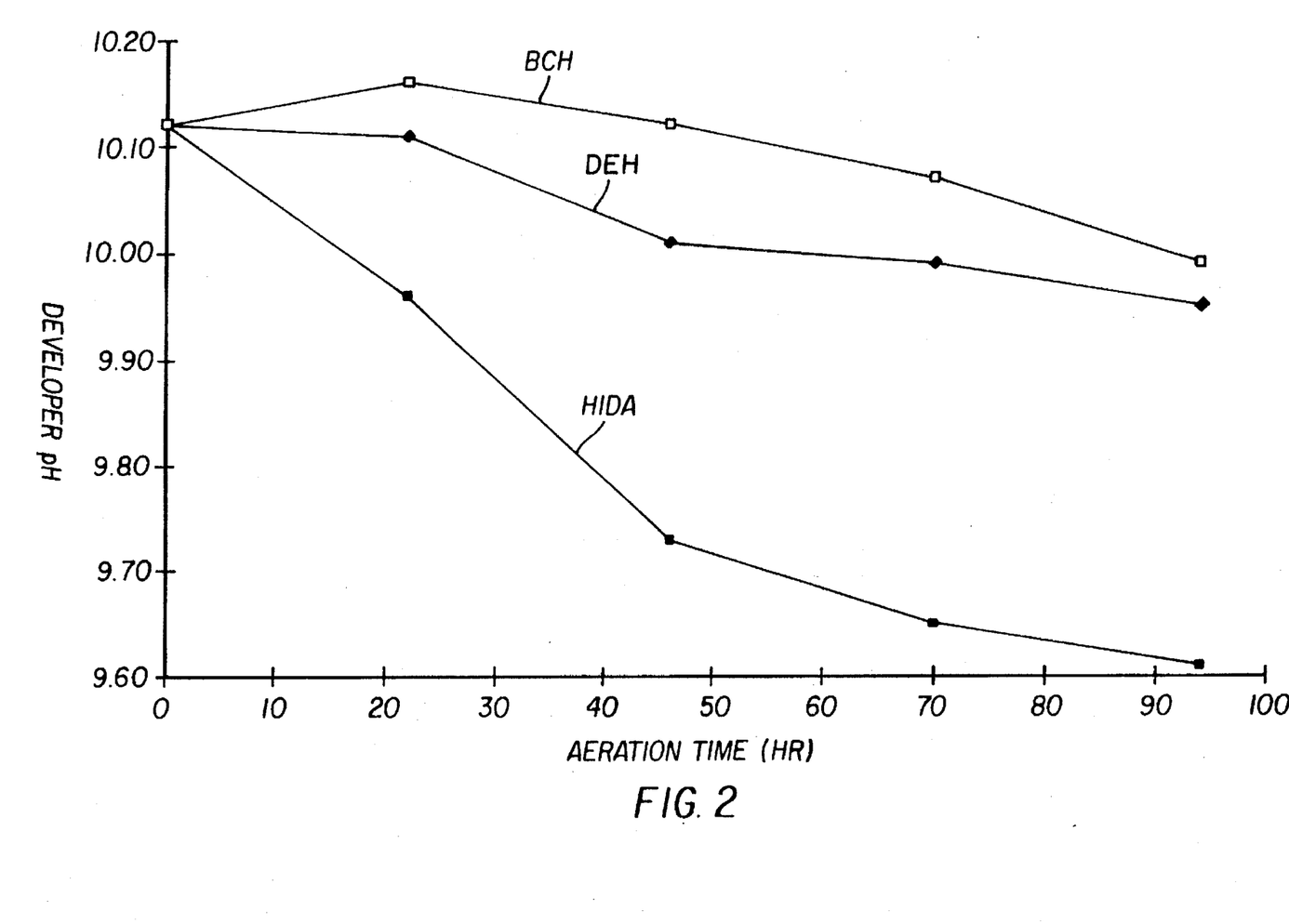
FIG. 2 depicts the effect over time that three different hydroxylamine antioxidants, HIDA, BCH, and DEH, have on the pH of an aerated developer solution.

Developer solutions employing HIDA, BCH, and DEH were subjected to an "aeration" test designed to measure the concentration of color developer as a function of time with the solution continuously aerated. The three developer solutions were examined simultaneously for comparison purposes. The results of the aeration experiment are shown in FIG. 1. The antioxidant BCH preserves color developer for a longer period of time than DEH, demonstrating it's superior preserving ability. During the time period of the aeration experiment, the developer solution pH was also monitored and the results are shown in FIG. 2. While HIDA appeared to preserve color developer better then BCH, it can be seen in FIG. 2 that the solution pH dropped significantly. Thus, BCH maintained a constantly of pH, indicating a very low rate of hydrolysis. It can be inferred from the constancy of pH that the benzyl substituents of BCH stabilize the nitrone form of BCH and that HIDA and DEH are not so stablilized.

Example 6

The developer formulations described in Example 3 were used to process a silver chloride photosensitive paper using a standard paper process. The results are shown in Table 3. The densitometry data show that the anti-oxidants presented in the present invention (BCH and HBC) have a much less detrimental effect on dye density than do BPH and DEH.

TABLE 3

| Hydroxylamine Anti-oxidant | Color Records | Dmin | Dmax |
|---|---|---|---|
| BCH | Red | 0.117 | 2.469 |
|  | Green | 0.098 | 2.636 |
|  | Blue | 0.077 | 2.113 |
| DEH | Red | 0.114 | 2.473 |
|  | Green | 0.098 | 2.474 |
|  | Blue | 0.075 | 2.010 |
| BPH | Red | 0.102 | 0.490 |
|  | Green | 0.083 | 1.102 |
|  | Blue | 0.079 | 0.589 |
| HBC | Red | 0.114 | 2.487 |
|  | Green | 0.097 | 2.540 |
|  | Blue | 0.075 | 2.021 |

Example 7

Figure 3:
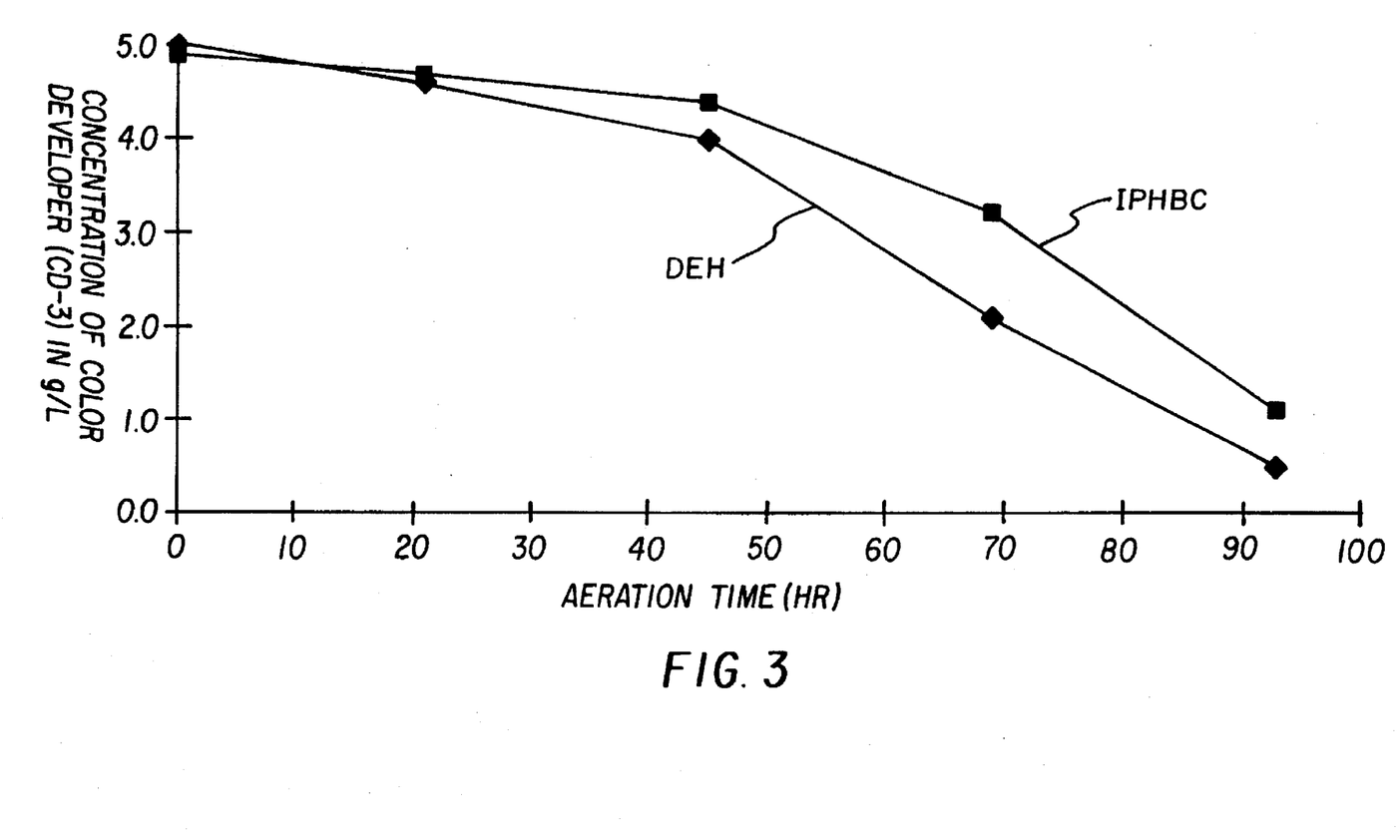
FIG. 3 depicts the effect over time that two different hydroxylamine antioxidants, IPHBC and DEH, have on the concentration of color developer contained in an aerated developer solution.
Figure 4:
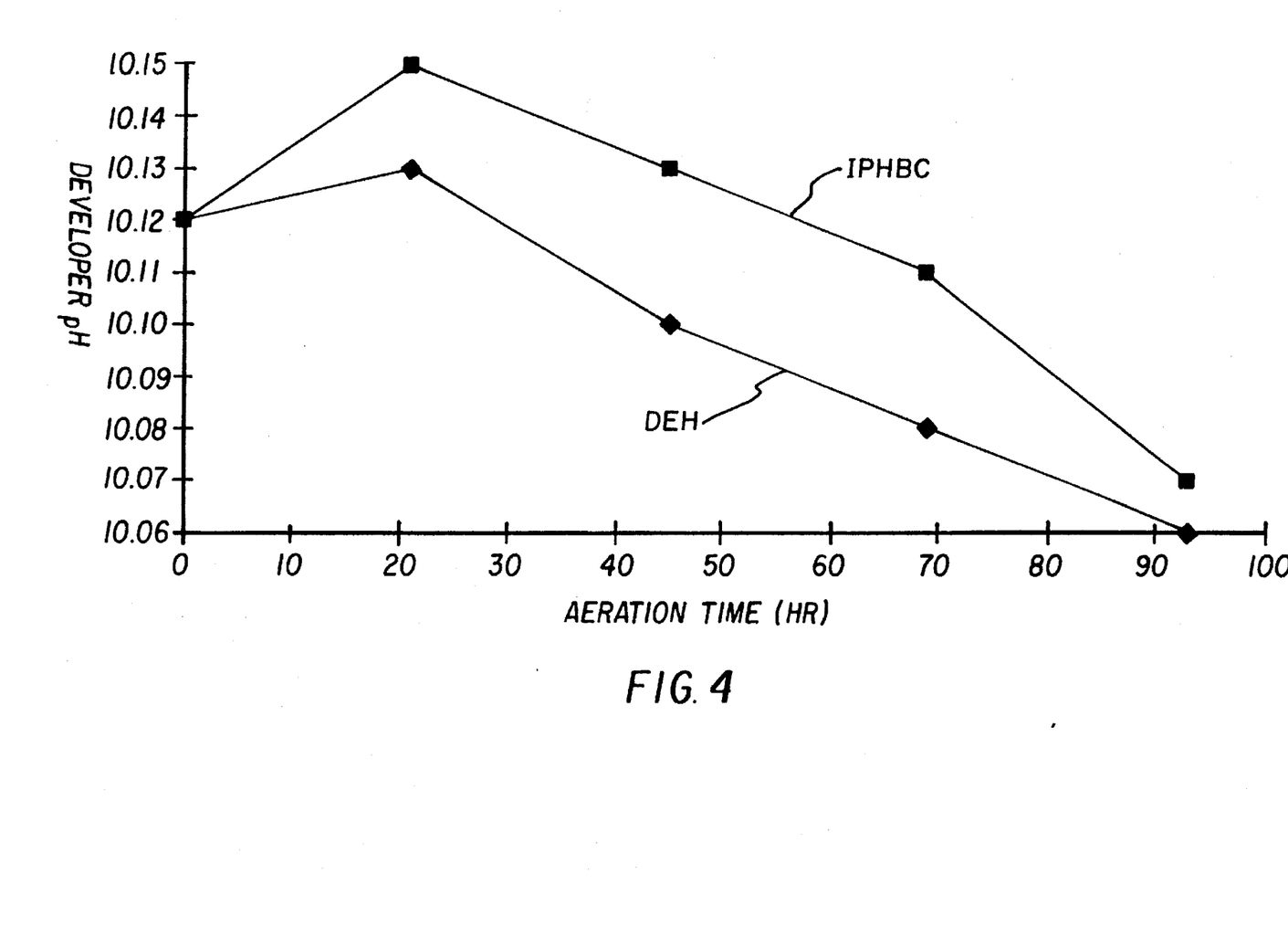
FIG. 4 depicts the effect over time that two different hydroxylamine antioxidants, IPHBC and DEH, have on the pH of an aerated developer solution.

A developer solution was formulated as in Example 5, with the exception of the anti-oxidant. In this example DEH was replaced with N-isopropyl-N-(4-carboxybenzyl)

hydroxylamine, and the molar concentration was changed from 0.050 to 0.040M. The solution was aerated as in Example 5 and the concentration of color developer (CD-3) and solution was measured as a function of aeration time. The results are shown in FIGS. 3 and 4. As the data show, N-isopropyl-N-(4-carboxybenzyl)hydroxylamine is better preservative for color developer than DEH, and maintains better control of developer pH.

TABLE 4

Concentration of CD-3 (g/L)

| Time (hr) | DEH | IPHBC |
| --- | --- | --- |
| 0 | 5 | 4.9 |
| 21 | 4.6 | 4.7 |
| 45 | 4 | 4.4 |
| 69 | 2.1 | 3.2 |
| 93 | 0.5 | 1.1 |

TABLE 5

Color Developer pH

| Time (hr) | DEH | IPHBC |
| --- | --- | --- |
| 0 | 10.12 | 10.12 |
| 21 | 10.13 | 10.15 |
| 45 | 10.1 | 10.13 |
| 69 | 10.08 | 10.11 |
| 93 | 10.06 | 10.07 |

The invention has been described in detail with particular reference to preferred embodiments thereof, but it will be understood that variations and modifications can be effected within the spirit and scope of the invention.

What is claimed is:

1. A composition for developing a silver halide color photographic material comprising a color developing agent and from 0.005 to 0.1M of a water-soluble hydroxylamine compound represented by Formula III or IV wherein X, $X^1$ and $X^2$ are independently —$CH_2OH$, —$SO_3M$, —$PO_3M$ or —COOM wherein M is an organic or inorganic cation or ester group;

$R^1$, $R^2$, $R^3$, $R^4$, $R^5$ and R6 are independently substituent groups;

m, n and r are independently 0 to 4 o, p and q are independently 0 to 2 and $R^7$ is a substituted or unsubstituted alkyl, aryl or heterocyclic group.

2. The composition of claim 1 wherein the hydroxylamine compound is represented by Formula III and X and $X^1$ are independently $SO_3M$, $PO_3M$ or COOM, wherein M is H or an alkali metal.

3. The composition of claim 2 wherein m, n, o and p are 0.

4. The composition of claim 2 wherein the hydroxylamine compound is N,N-bis(p-carboxybenzyl)hydroxylamine.

5. The composition of claim 1 wherein the hydroxylamine compound is represented by Formula IV; wherein $X^2$ is —$CH_2OH$, —$SO_3M$, —$PO_3M$ or —COOM; M is H or an alkali metal; and $R^7$ is a substituted or unsubstituted alkyl group of 1 to 10 carbon atoms, a substituted or unsubstituted aryl group of 6 to 10 carbon atoms, or a substituted or unsubstituted 5 to 6 membered heterocyclic group containing one or two heteroatoms.

6. The composition of claim 5 wherein $X^2$ is —COOH; q is 0; r is 0; and $R^7$ is a substituted or unsubstituted straight or branched alkyl group of 1 to 6 carbon atoms or a substituted or unsubstituted phenyl group.

7. The composition of claim 5 wherein the hydroxylamine compound is N-methyl-N-p-carboxybenzylhydroxylamine.

8. The composition of claim 1 wherein said hydroxylamine is present in said color developer in an amount of from 0.025 to 0.05M.

9. The composition of claim 1 having a pH of from 9 to 13.

10. The composition of claim 9 having a pH of from 9 to 11.

11. The composition of claim 10 having a pH of from 9.9 to 10.2.

12. The composition of claim 1 further comprising a metal ion sequestering agent, or an alkali metal halide.

13. The composition of claim 1 wherein $R^2$, $R^3$ and $R^5$ are independently unsubstituted phenyl or alkyl group of 1 to 6 carbon atoms, or phenyl or an alkyl group of 1 to 6 carbon atoms substituted with a solubilizing group.

14. The composition of claim 13 wherein $R^2$, $R^3$ and $R^5$ are independently isopropyl, benzyl, t-butyl or —$CH_2COOR^8$ wherein $R^8$ is hydrogen or an alkali or alkaline earth metal cation.

15. The composition of claim 1 wherein $R^7$ is unsubstituted alkyl of 1 to 6 carbon atoms or an alkyl group of 1 to 6 carbon atoms substituted with a solubilizing group.

16. The composition of claim 15 wherein $R^7$ is methyl, ethyl, isopropyl, t-butyl, —$(CH_2)$—$COOR^8$, —$CH_2CH_2OH$ or —$CH_2COOR^8$ wherein $R^8$ is hydrogen or an alkali or alkaline earth metal cation.

17. The composition of claim 1 wherein said hydroxylamine is N-methyl-N-(p-carboxybenzyl)hydroxylamine, N-isopropyl-N-(p-carboxybenzyl)hydroxylamine, N,N-bis(p-carboxybenzyl)hydroxylamine, N,N-bis(4-hydroxymethylbenzyl)hydroxylamine, N-(4-hydroxymethylbenzyl)-N-isopropylhydroxylamine or N-(4-hydroxymethylbenzyl)-N-methylhydroxylamine.

18. A method for processing a color photographic element comprising:

treating an imagewise exposed color photographic silver halide element with a color developer composition comprising a color developing agent and from 0.005 to 0.1 M of a water-soluble hydroxylamine compound represented by Formula III or IV -continued

IV wherein X, X$^1$ and X$^2$ are independently —CH$_2$OH, —SO$_3$M, —PO$_3$M or —COOM wherein M is an organic or inorganic cation or ester group;

R$^1$, R$^2$, R$^3$, R$^4$, R$^5$ and R6 are independently substituent groups;

m, n and r are independently 0 to 4 o, p and q are independently 0 to 2 and

R$^7$ is a substituted or unsubstituted alkyl, aryl or heterocyclic group.

19. The method of claim 18 carried out in a low volume thin tank processor comprising a narrow processing channel that has an opening for delivering said color developer composition to said narrow processing channel according to the equation:

$$1 \leq F/A \leq 40$$

wherein F is the flow rate of said color developer composition through said opening in gallons per minute, and A is the cross-sectional area of said opening in square inches.

* * * * *